US010317372B2

(12) United States Patent
Carrasco Zanini et al.

(10) Patent No.: US 10,317,372 B2
(45) Date of Patent: *Jun. 11, 2019

(54) DEPLOYMENT MECHANISM FOR PASSIVE NORMALIZATION OF A PROBE RELATIVE TO A SURFACE

(71) Applicants: Saudi Arabian Oil Company, Dhahran (SA); HiBot Corporation, Meguro-ku, Tokyo (JP)

(72) Inventors: Pablo Carrasco Zanini, Thuwal (SA); Fadl Abdellatif, Thuwal (SA); Sahejad Patel, Thuwal (SA); Shigeo Hirose, Tokyo (JP); Michele Guarnieri, Tokyo (JP); Paulo Debenest, Tokyo (JP)

(73) Assignees: HIBOT CORPORATION, Tokyo (JP); SAUDI ARABIAN OIL COMPANY, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/996,102

(22) Filed: Jun. 1, 2018

(65) Prior Publication Data
US 2018/0275102 A1    Sep. 27, 2018

Related U.S. Application Data

(63) Continuation of application No. 14/624,726, filed on Feb. 18, 2015, now Pat. No. 10,012,618.

(51) Int. Cl.
*G01N 29/24* (2006.01)
*G01N 29/22* (2006.01)
(Continued)

(52) U.S. Cl.
CPC ......... *G01N 29/2487* (2013.01); *B62D 63/02* (2013.01); *G01N 29/225* (2013.01);
(Continued)

(58) Field of Classification Search
CPC .. G01N 29/225; G01N 29/226; G01N 29/265; G01N 29/2487; G01N 29/2493;
(Continued)

(56) References Cited

U.S. PATENT DOCUMENTS 4,421,118 A    12/1983    Dow et al.
4,995,320 A    2/1991    Sato et al.
(Continued)

FOREIGN PATENT DOCUMENTS

DE    10 2012 208095    11/2013
EP    2 662 689    11/2013
(Continued)

OTHER PUBLICATIONS

Silverwing, "UT Lite Family: Manual Ultrasonic Corrosion Profiling, Mapping and Weld Flaw Detection." UT Lite—Corrosion Profiling—Corrosion Mapping—Weld Flaw Detection: pp. 1-4. 2015.
(Continued)

*Primary Examiner* — Justin Seo
*Assistant Examiner* — Rose M Miller
(74) *Attorney, Agent, or Firm* — Leason Ellis LLP

(57) ABSTRACT

The present apparatus is configured to carry an instrument or probe and optionally deploy it against a surface, such as a metal pipeline or storage tank. The apparatus can include a sensor probe for inspecting the integrity of the surface and a first linkage that is operatively coupled to the sensor probe and configured to move the sensor probe according to a first path (in a first direction/first degree of freedom). An actuator can be operatively connected to the first linkage for moving the first linkage so as to move the sensor probe along the first path. A second linkage is operatively connected to the sensor probe and configured to passively move the sensor probe according to a second degree of freedom to cause the sensor
(Continued)

probe to become normal to the surface when at least a portion of the apparatus contacts the surface.

19 Claims, 12 Drawing Sheets

(51) Int. Cl.
*G01N 29/265* (2006.01)
*B62D 63/02* (2006.01)

(52) U.S. Cl.
CPC ......... *G01N 29/226* (2013.01); *G01N 29/265* (2013.01); *G01N 2291/02854* (2013.01); *G01N 2291/263* (2013.01); *G01N 2291/2634* (2013.01)

(58) Field of Classification Search
CPC ..... G01N 2291/263; G01N 2291/2634; G01N 2291/2638; G01N 2291/02854; G01N 2291/0234; G01N 2291/0232; B62D 63/02
USPC ......... 73/632, 618, 619, 621, 622, 633, 634, 73/635, 639
See application file for complete search history.

(56) References Cited

U.S. PATENT DOCUMENTS

| | | | |
|---|---|---|---|
| 5,332,143 A | 7/1994 | Furukawa | |
| 5,741,973 A | 4/1998 | Clark | |
| 6,341,525 B1* | 1/2002 | Takada | B24B 27/033 73/584 |
| 7,604,645 B2 | 10/2009 | Barzell et al. | |
| 10,012,618 B2* | 7/2018 | Carrasco Zanini | G01N 29/2487 |
| 2006/0055399 A1 | 3/2006 | Georgeson | |
| 2008/0087112 A1 | 4/2008 | Bagley et al. | |
| 2010/0204578 A1 | 8/2010 | Schmidt et al. | |
| 2011/0041612 A1 | 2/2011 | Paige | |
| 2012/0253696 A1 | 10/2012 | Pearson et al. | |
| 2013/0250719 A1 | 9/2013 | Kollgaard | |
| 2013/0304251 A1 | 11/2013 | Garvey | |
| 2014/0200832 A1 | 7/2014 | Troy | |
| 2014/0305217 A1 | 10/2014 | Tapia | |
| 2015/0053015 A1* | 2/2015 | Sarr | G01N 29/24 73/632 |
| 2015/0226369 A1 | 8/2015 | Troy | |

FOREIGN PATENT DOCUMENTS

| | | |
|---|---|---|
| JP | S58-38855 | 3/1983 |
| JP | S58-63848 | 4/1983 |
| JP | S64-15651 | 1/1989 |
| JP | H02-67958 | 3/1990 |
| JP | H02-74272 | 6/1990 |
| JP | H05-8415 | 2/1993 |
| JP | 2003-172731 | 6/2003 |
| WO | WO 2012/126559 | 9/2012 |

OTHER PUBLICATIONS

Silverwing NDT. "Scorpion B-Scan—Remote Access, Dry Coupled, B-Scan Ultrasonic Crawler." YouTube. YouTube, Jun. 8, 2011. Web. <https://www.youtube.com/watch?v=rEcEB49JM6A>.
Silverwing, "Scorpion: Remote Access Crawler With a Dry Coupled Wheel Probe for UT Thickness Measurements." Scorpion: Remote Access Ultrasonic Crawler: pp. 1-4. 2015.

* cited by examiner

Fig. 9A 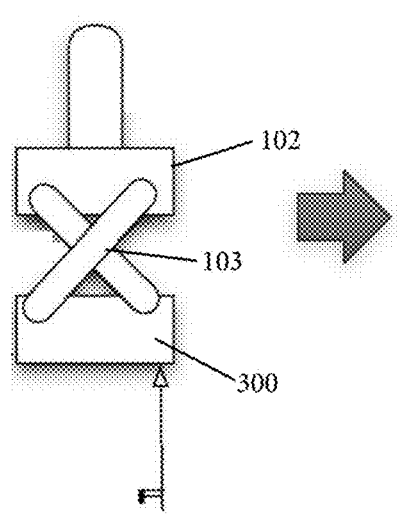 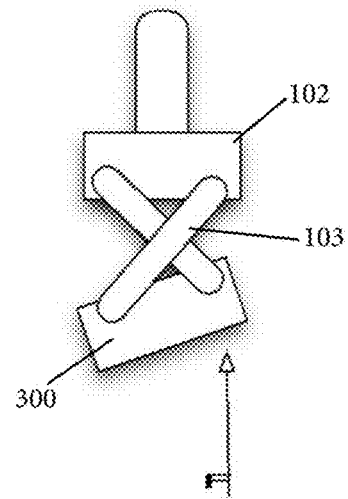 Fig. 9B
Fig. 10A 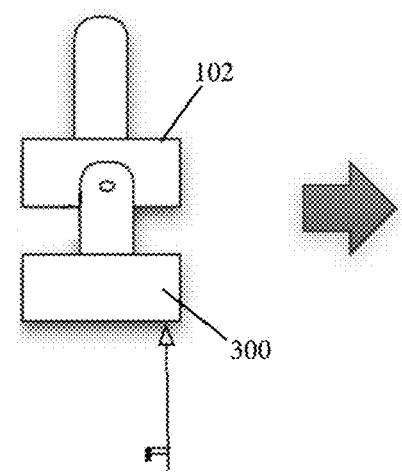 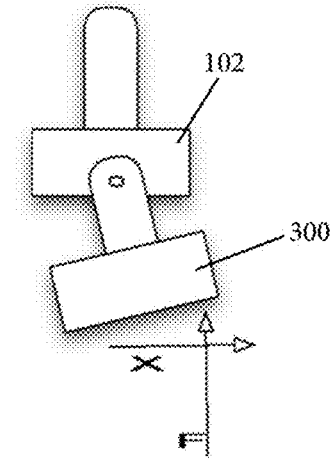 Fig. 10B

DEPLOYMENT MECHANISM FOR PASSIVE NORMALIZATION OF A PROBE RELATIVE TO A SURFACE

CROSS-REFERENCE TO RELATED PATENT APPLICATIONS

This application is a continuation of U.S. patent application Ser. No. 14/624,726, filed Feb. 18, 2015, the entire contents of which is incorporated by reference herein as if expressly set forth in its respective entirety herein.

TECHNICAL FIELD

The present invention relates to an apparatus for supporting an instrument, such as a sensor (e.g., ultrasonic probe) and more particularly, to an apparatus that is configured to carry the sensor such that the sensor can be lowered or deployed against a surface (e.g., a pipe wall) and automatically become at least substantially normal to the surface upon contact between at least a portion of the apparatus and the surface.

BACKGROUND

Routine inspection of equipment is critical in most industries in order to ensure safety and optimize performance. For example, in the petroleum industry and related fields, liquids and gases and mixtures thereof are transported via pipelines and these materials are also stored in large tanks.

It is known in this industry that in order to maintain the integrity of pipelines, storage tanks and the like, a sensor device can be employed to inspect such surfaces. In particular, an inspection vehicle can be used to travel across a surface of the target object (e.g., a pipe or tank) and record information about the quality of the pipe wall. A majority of these inspection vehicles use ultrasonic or magnetic sensors to carry out the inspection. Based on the recorded information, any cracks or other deficiencies in the surface being inspected (e.g., pipe wall) can be detected and noted to allow for subsequent remedial action to be taken.

While there are a number of different sensors that can be used in such inspection vehicles, one preferred type of ultrasonic sensor is a dry coupled probe (DCP) that is configured to perform ultrasonic inspection of the surface to measure wall thickness and detect corrosion. Dry coupled probes are typically built in the form of a wheel in which a shaft (axle) is meant to be held fixed since the shaft has the transducer component rigidly embedded in it while an outer tire rotates around the shaft. The shaft of the probe thus must be held and positioned such that the transducer always points at the surface, meaning that the wheel is not titled in its roll and pitch directions.

Thus, one of the challenges in using a DCP is that the probe needs to always be perpendicular (normal) to the surface being inspected and this can be a challenge while the inspection vehicle is mobile and navigating the surface. This is especially difficult since the inspection vehicle can drive circumferentially, longitudinally and helically on a pipe or tank surface which means that the DCP has to be realigned to ensure that the DCP is normal to the surface being inspected regardless of the location of the inspection vehicle.

The present invention is thus directed to a mechanism (device/apparatus) that both normalizes the sensor (e.g., DCP) and also allows the sensor to be lifted off the surface being inspected when inspection is not being performed to avoid unnecessary wear mainly while the inspection vehicle is being steered and/or moved to a different inspection location.

SUMMARY

The present apparatus is configured to carry an instrument/probe which is configured to inspect a surface, such as a metal pipeline or storage tank, and the apparatus is also configured to be coupled to an inspection vehicle. The instrument can be in the form of a sensor probe, such as one that is configured to inspect the integrity of the surface and a first linkage that is operatively coupled to the sensor probe and configured to move the sensor probe according to a first degree of freedom. An actuator can be operatively connected to the first linkage for moving the first linkage so as to move the sensor probe according to the first degree of freedom. A second linkage is operatively connected to the sensor probe and configured to passively move the sensor probe according to a second degree of freedom to cause the sensor probe to become at least substantially normal to the surface upon contact between at least a portion of the apparatus (e.g., the second linkage) and the surface. The first degree of freedom can be an up and down movement (e.g., the sensor can move in an up and down direction but along a slightly curved path) (which can be generally thought of as a pitch direction) to allow a lowering (deployment) and raising of the sensor probe and the second degree of freedom can be motion in a roll direction. Thus, the first degree of freedom is not limited to movement in only a linear direction but can include a curved path.

The first linkage can be an active mechanism in that the first linkage is driven by operation of the actuator; however, the second linkage is a passive mechanism in that the second linkage automatically normalizes the sensor probe when it is deployed and at least a portion of the apparatus (e.g., the second linkage) contacts the surface. However, in an alternative embodiment, the device does not include an actuator and the probe is always deployed against the surface. In this alternative embodiment, a biasing member, such as a spring, can be used to hold the probe against the surface to provide some dampening/suspension.

It will thus be understood that the normalization that is discussed herein occurs when at least a portion of the apparatus makes contact with the surface. For example, the portion of the apparatus that makes contact can be in the form of the second linkage and may or may not include the object that is being carried by the apparatus (i.e., the sensor (probe)). For example, in some embodiments, it is not desirable for the carried object (e.g., an imaging device (camera) or laser instrument) to make physical contact with the surface. Instead, in these embodiments, the object remains suspended by the apparatus (e.g., the second linkage) and slightly spaced from the surface, while another portion of the apparatus, such as the second linkage, is in contact with the surface.

This mechanism provided by the present invention is particularly useful for sensitive directional sensors, such as a dry coupled probe which requires having its internal transducer component be always normal to the inspected surface in order to have proper readings from it.

BRIEF DESCRIPTION OF THE DRAWING FIGURES

FIG. 9A is a schematic showing the second linkage in a first state;

FIG. 9B is a schematic showing the second linkage in a second state after a force has been applied thereto;

FIG. 10A is a schematic showing a conventional T linkage in a first state;

FIG. 10B is a schematic showing the conventional T linkage in a second state after a force has been applied thereto;

Figure 12A:
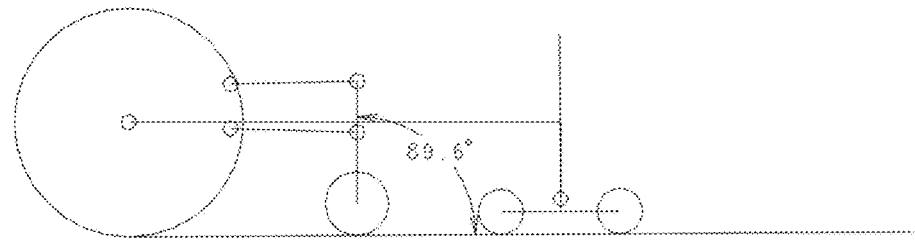
FIG. 12A is a side elevation view of the sensor probe on a flat surface illustrating that the contact angle between the probe and the surface can be at least substantially normal due to the construction of the present invention.
Figure 12B:
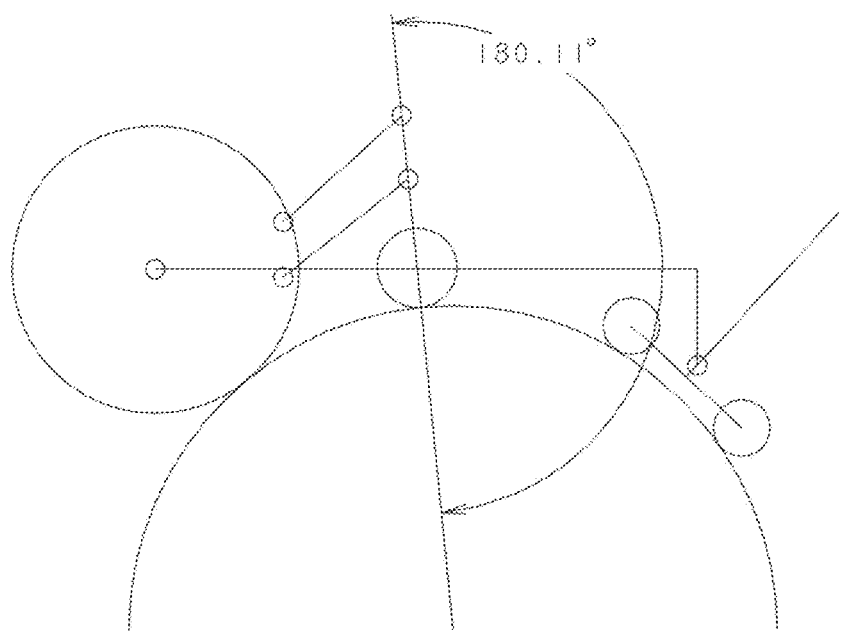
Figure 12C:
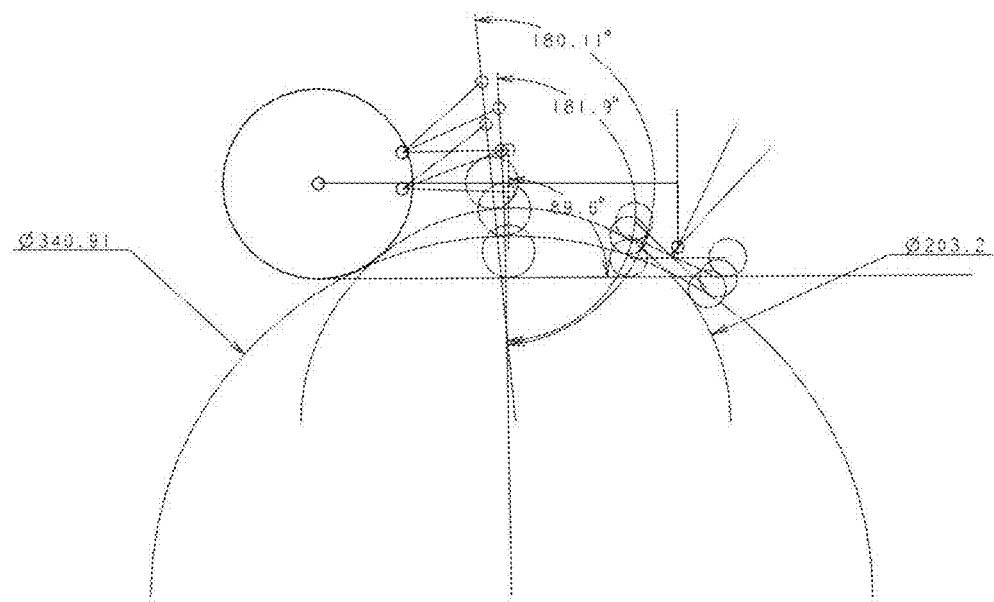

FIG. 12B is a side elevation view of the sensor probe on an 8 inch pipe illustrating that the contact angle between the probe and the surface can be at least substantially normal due to the construction of the present invention; and FIG. 12C is a side elevation view of the sensor probe on a 13 inch pipe illustrating that the contact angle between the probe and the surface can be at least substantially normal due to the construction of the present invention.

DETAILED DESCRIPTION OF CERTAIN EMBODIMENTS

Figure 1:
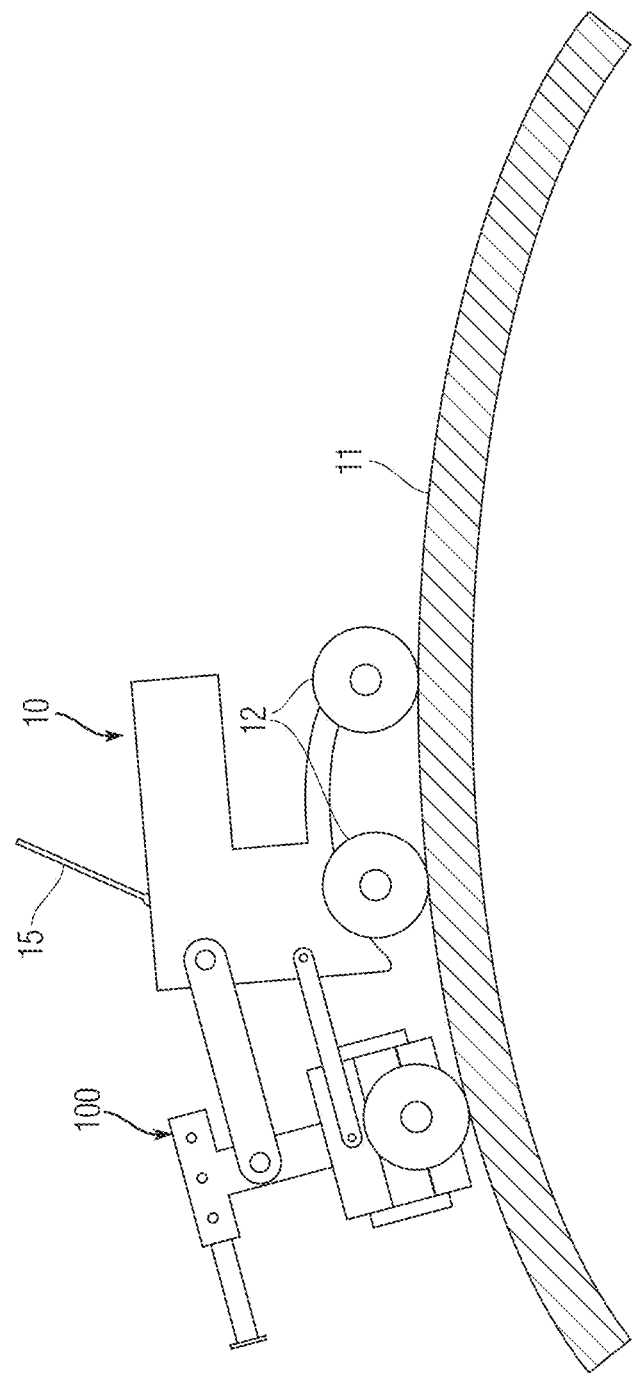
FIG. 1 is side view of an external device, such as an inspection vehicle, with a device for carrying a sensor probe in accordance with the present invention.

FIG. 1 generally shows an external device 10 and an apparatus (mechanism) 100 which is configured to be releasably coupled to an external device 10 and to carry a probe sensor such that the sensor can be lowered or deployed against a surface 11, such as a surface of a pipe or storage tank, and automatically become normal to the surface 11 upon contact between at least a portion of the apparatus 100 and the surface. As described herein, it will be appreciated that the external device 10 does not necessarily have to make contact with the surface but instead, one or more parts of the apparatus 100 can make contact.

The external device 10 can be in the form of an inspection vehicle (such as a robot as shown herein), handheld carrier, a robotic arm gripper, a PIG or scrapper for in-pipe inspection, etc. In other words, the apparatus 100 can be coupled to any number of different pieces of equipment depending upon the particular application. For example, the apparatus 100 can be coupled to a handheld carrier and as described herein, the design of the apparatus 100 allows for the apparatus 100 to follow helical patterns which other handheld carriers are not able to do. The coupling of the apparatus 100 to a robotic arm gripper for automated selective inspection of pipes, beams and sheet metal or cast iron parts at a foundry or factory. For purpose of illustration only, the apparatus 100 is described and shown as being attached to an inspection vehicle 10; however, it will be understood that, as mentioned above, the apparatus 100 can be attached to other external pieces of equipment. Thus, the description and illustration of the apparatus 100 being attached to the inspection vehicle 10 is not limiting of the scope of the present invention.

The inspection vehicle 10 can be any number of different vehicles that can be controllably driven across the surface 11. For example, the inspection vehicle 10 can be a robotic device that can be controlled by a user who can transmit control commands to the inspection vehicle 10 to control the operation of the inspection vehicle 10. In this manner, the user can effectively drive the robotic inspection vehicle 10 across the surface and can stop and steer the vehicle 10 as well. As described below, the information that is captured and recorded by the apparatus 100 can be transmitted to the user using suitable communications protocol including both wired and wireless communications (wireless antenna 15). The robotic inspection vehicle 10 can thus be a vehicle that has two or more wheels 12 that allow the robotic inspection vehicle 10 to be driven across the surface 11. The wheels 12 can be formed of a magnetic material to allow the robotic inspection vehicle 10 to attach to a metal surface 11, such as a metal pipe or metal storage tank and be movable thereacross. The robotic inspection vehicle 10 further includes other operating parts including a motor for controlling rotation of the wheels and a steering mechanism as well as a processor that is configured to generate user commands to operate the vehicle 10 and also to receive and record the information received from the sensor.

The details of the apparatus 100 are best appreciated in view of FIGS. 2-6. The apparatus 100 includes a number of components that can be thought of as being different sub-assemblies that mate together to form the apparatus 100 (after assembly, the apparatus 100 is in the form of a single structure shown in FIG. 2). In particular, the apparatus 100 can be thought of as including a drive assembly 101 (drive component); a first linkage 102, a second linkage 103, and a sensor probe structure 104. As described herein, the apparatus 100 is configured to be attachably coupled to the inspection vehicle 10 since the inspection vehicle 10 provides the means for moving the apparatus 100 across the surface 11 for inspection of one or more regions of the surface 11.

The drive component 101 of the apparatus 100 comprises an actuator which is intended to operate on the first linkage 102 for controlled movement thereof as described herein. In the illustrated embodiment, the drive component 101 includes a motor 110 and a transmission 150 that is operatively connected to the motor 110 and the first linkage 102. The motor 110 can be any number of different types of motors that are suitable for use in the present application. For example, the motor 110 can be a brushless DC motor that can be controlled using a user interface (such as a master controller which is located remote from the vehicle and controlled by a user). The motor 110 has a rotatable drive shaft 112 and is connected to a power source, such as a battery pack. The motor 110 is also securely attached to a motor mount 130 that includes an opening for receiving the motor 110 (which can have an elongated shape as shown) and has a mounting surface 131 which can be a planar surface.

The rotation of the drive shaft 112 of the motor 110 is translated into movement of the first linkage 101 by means of the transmission 150. In accordance with one embodiment, the transmission 150 is in the form of a worm drive assembly which as is known is a type of gear arrangement. More particularly, the worm drive assembly includes a worm 152 (which is a gear in the form of a screw) which meshes with a worm gear 154 (which is similar in appearance to spur gear and is also called a worm wheel). The worm 152 is fixedly coupled to the drive shaft 112 or is an integral part thereof such that actuation (operation) of the motor 110 causes rotation of the drive shaft 112 and the worm 152. The drive shaft 112 and worm 152 are thus coaxial and rotate about a first axis. The drive component 101 can also include an end cap 155 and a bearing 157 or the like which rotatably support the worm 152.

The worm gear 154 is fixedly coupled to a worm gear shaft 159 which extends along a second axis that is perpendicular to the first axis. As described in detail below, the worm gear 154 and shaft 159 are coupled to the first linkage 101 so as to position the worm gear 154 is meshed relationship with the worm 152. Rotation of the worm 152 is translation into rotation of the worm gear 154. The shaft 159 is fixedly attached at its first end to the worm gear 154.

The first linkage 102 consists of a number of parts that form the linkage and provide a means for attaching the apparatus 100 to the inspection vehicle 10 and also provide a means for supporting the drive component 101. The first linkage 102 includes a first linkage plate 160, a second linkage plate 180 that is spaced from the first linkage plate 160, a first connector arm 190, and a second connector arm 200. In one embodiment, the first and second connector arms 190, 200 can have different lengths. This feature is described below with reference to FIGS. 12A-C.

The first linkage plate 160 can be a planar structure that has a first end (top end) 162 and an opposing second end (bottom end) 164. The first linkage plate 160 has an enlarged first section (angled section) 163 at the first end 162 and an enlarged second section (horizontal section) 165 at the second end 164 with a narrow intermediate section (vertical section) 166 formed between the first section 163 and the second section 165. The illustrated first and second sections 163, 165 have generally rectangular shapes with the first section 163 being formed at an angle relative to the second section 165. The narrow intermediate section 166 serves to space the first section 163 from the second section 165 and is oriented perpendicular to the second section 165.

The first section 163 is sized and shaped to mate with the mounting surface 131 of the mount 130. The first section 163 includes a plurality of through holes 167 that receive fasteners 169 for attaching the first section 163 to the mount surface 131 of the mount 130. In this manner, motor 110, worm 152 and mount 130 which define the drive component 101 are fixedly attached and supported by the first linkage plate 160.

The narrow intermediate section 166 includes a first through hole 170, a second through hole 172 and a third through hole 174. The through holes 170, 172, 174 are formed in a linear manner with the first through hole 170 being the topmost hole, the second through hole 172 being the middle hole and the third through hole 174 being the bottommost hole. The shaft 159 extends through the first through hole 170 and freely rotates therein.

The second section 165 includes a first end surface 175 and an opposite second end surface 177.

The second linkage plate 180 has a first end (top end) 182 and an opposing second end (bottom end) 184. The second linkage plate 180 includes a first vertical section 183 that terminates at the first end 182 and a second horizontal section 185 at the second end 184. The first vertical section 183 and the second horizontal section 185 are sized and shaped so as to be complementary to the narrow intermediate section 166 and the second section 165. More specifically, the second horizontal section 185 can be identical to the second section 165. The first vertical section 183 includes three through holes formed therein, namely, a first through hole 186, a second through hole 187, and a third through hole 188. The through holes 186, 187, 188 are formed such that they axially align with the through holes 170, 172, 174, respectively, formed in the first linkage plate 160.

The second horizontal section 185 includes a first end surface 181 and an opposite second end surface 189.

The shaft 159 passes through the through hole 170 and the through hole 186 with the shaft 159 being freely rotatable relative to the first linkage plate 160 and the second linkage plate 180.

As shown, the first and second linkage plates 160, 180 are positioned in parallel planes that are spaced apart from one another. More specifically, the first linkage plate 160 and the second linkage plate 180 are fixedly connected to one another to maintain the fixed spaced relationship and to prevent movement therebetween. The first and second linkage plates 160, 180 can be connected by a connector 135 that has an elongated shape and can be in the form of a rod that is fixedly connected at one end to the first linkage plate 160 (as by a fastener) and at its opposite end to the second linkage plate 180 (as by a fastener). The two ends of the connector 135 can be inserted into the holes 172, 187.

The first and second linkage plates 160, 180 define a first link of the first linkage 102.

The first connector arm 190 and the second connector arm 200 are in the form of structures that are each pivotally connected to both the first link (the first and second linkage plates 160, 180) and the inspection vehicle 10. As shown in the figures, the first connector arm 190 is located above the second connector arm 200. The first connector arm 190 has a base portion 191 (e.g., a horizontal bar) and a first pair of arms (flanges) 192 that extend outwardly from the base portion 191 at opposing ends thereof. The first pair of arms 192 are oriented perpendicular to the base portion 191 and are disposed in parallel planes such that in combination with the base portion 191, a first U-shaped structure is defined. The free ends of the arms 192 receive fasteners 193 for pivotally attaching the arms 192 to a body of the inspection vehicle 10. This allows the first connector arm 190 to pivot about the body of the inspective vehicle 10.

The first connector arm 190 also includes a plurality of arms that extend inwardly from the base portion 191 and locations intermediate the two ends of the base portion 191. As shown in the figures, a first inner arm 194 is formed proximate one end of the base portion 191 and second and third inner arms 195, 196 are formed proximate the other end of the base portion 191. The second and third inner arms 195, 196 are formed proximate one another so as to define a space or slot 197 therebetween. The first, second, and third inner arms 194, 195, 196 are formed perpendicular to the base portion 191 and are located in parallel planes. The planes that contain the first pair of arms 192 and the arms 194, 195, 196 can be parallel to one another.

The free ends of the inner arms 194, 195, 196 include through holes which receive the shaft 159. The shaft 159 freely rotates relative to these arms 194, 195, 196 and also, as mentioned previously, freely rotates relative to the first linkage plate 160 and the second linkage plate 180.

When the first connector arm 190 is assembled to the first and second linkage plates 160, 180, the first vertical section 183 of the second linkage plate 180 is received within the slot 197 so as to position the first vertical section 183 between the arms 195, 196. The narrow intermediate section 166 of the first linkage plate 160 is positioned adjacent and inside of the arm 194. Once again, the shaft 159 extending through these parts serves to couple all of the parts together but in a manner in which the shaft 159 freely rotates.

The end of the shaft 159 that is opposite the worm gear can be received with a bearing member or the like 161 which is received within a recess formed along an outer surface of the arm 196. The bearing member 161 can have a circular shape. In addition, an end cap or fastener 137 can be used to prevent lateral movement of the shaft 159. In particular, a bolt 137 can be threadingly attached to the free end of the shaft 159 adjacent the bearing member 161, thereby restricting the lateral movement of the shaft 159.

Figure 4:
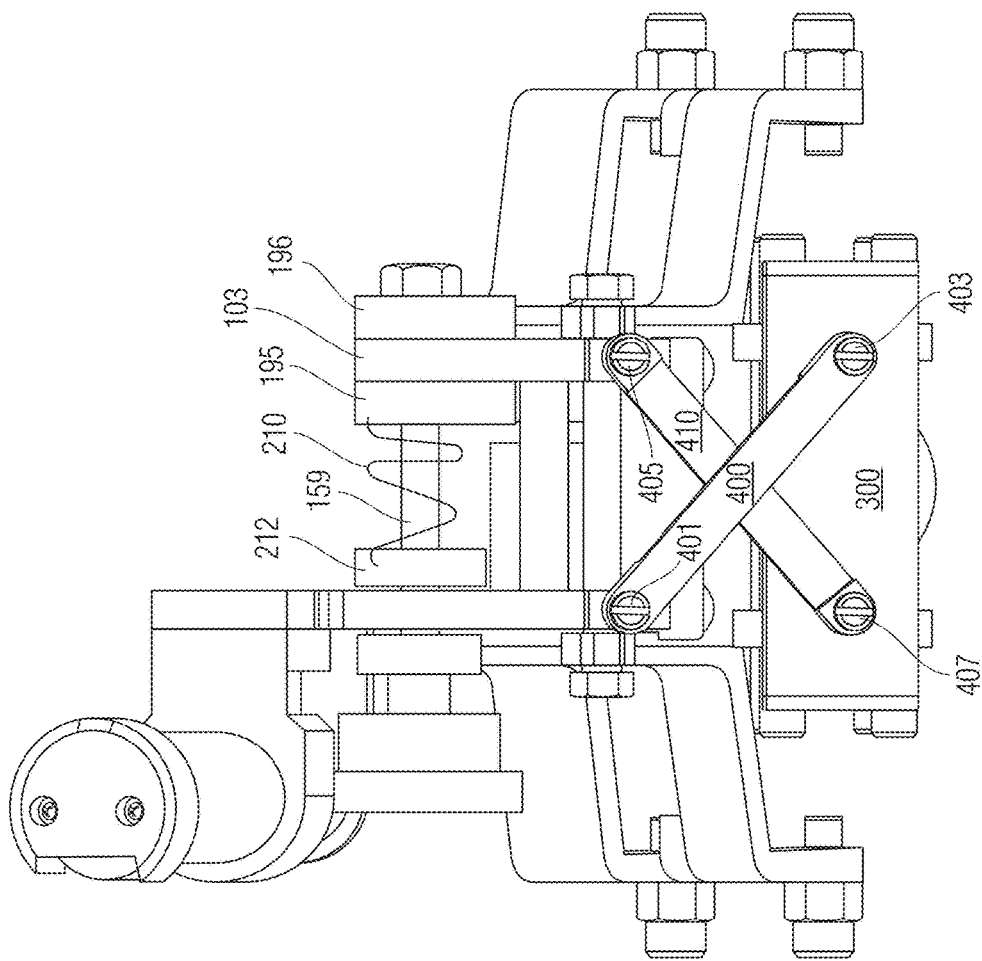
FIG. 4 is a front elevation view of the device of FIG. 1 showing a second linkage.
Figure 5:
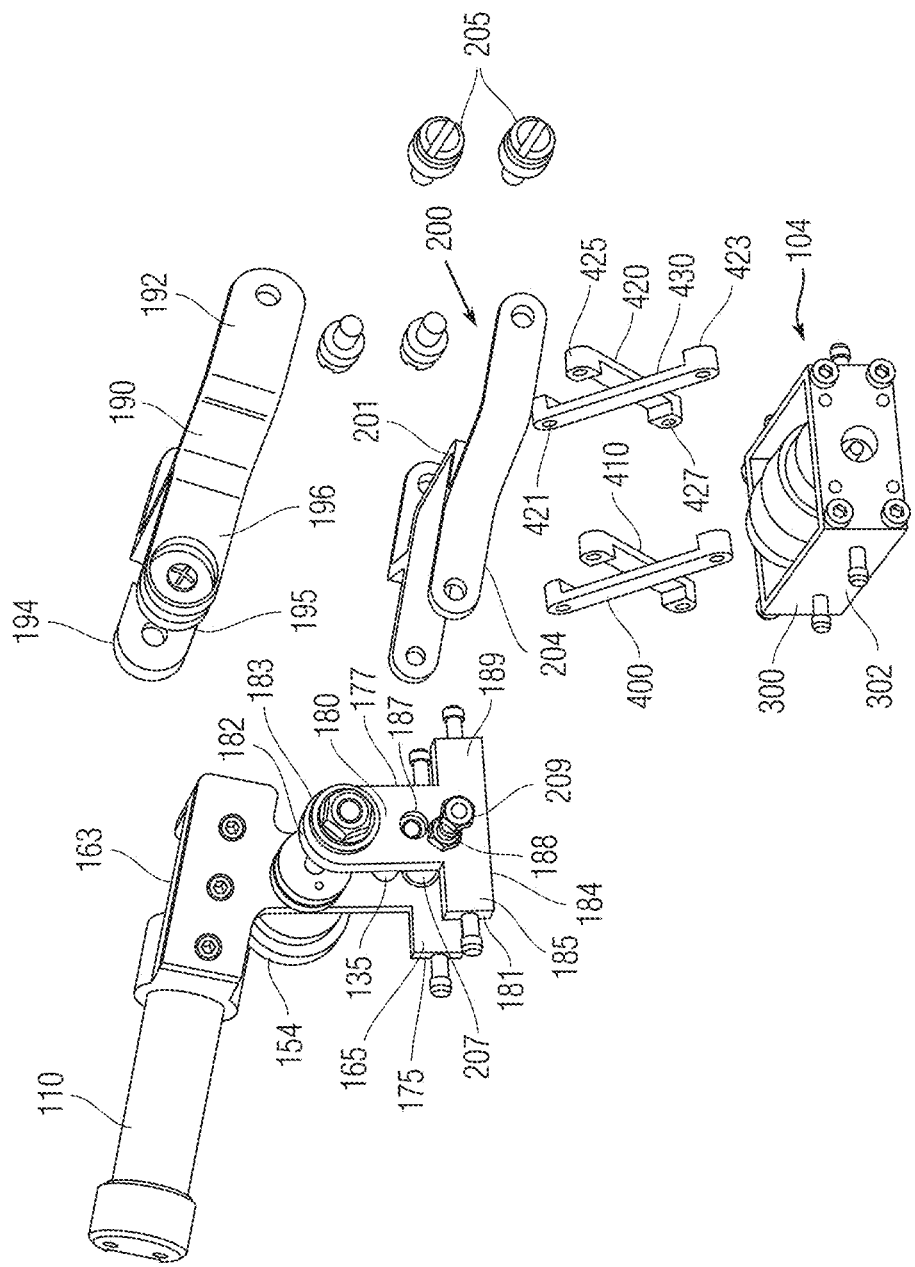
FIG. 5 is an exploded perspective view of the device of FIG. 1.
Figure 6:
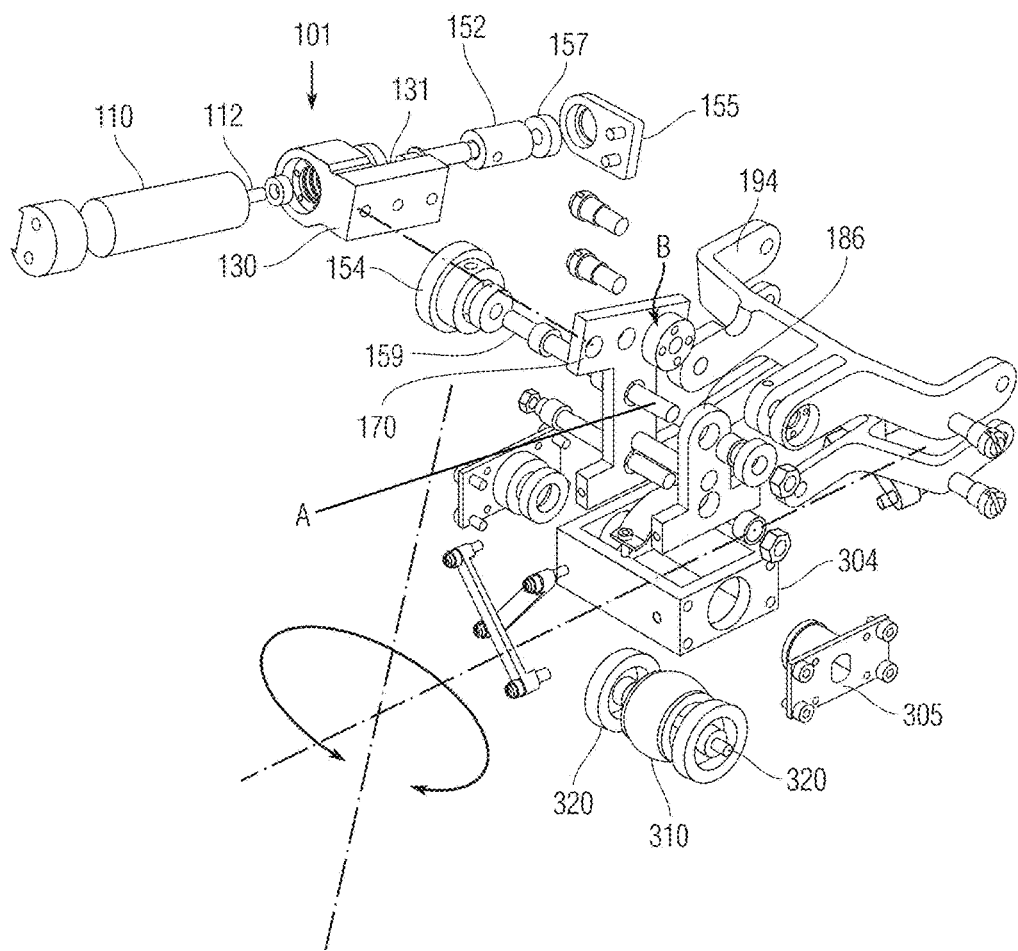
FIG. 6 is another exploded perspective view of the device of FIG. 1.
Figure 8:
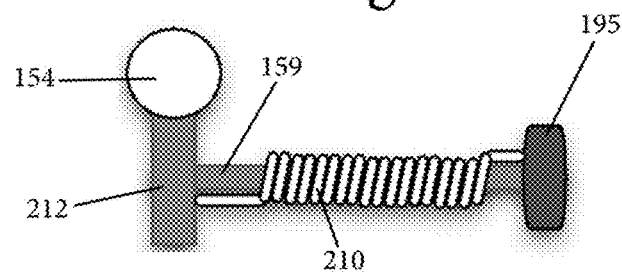
FIG. 8 is a front elevation view of a portion of a transmission of the device of FIG. 1 according to a second embodiment.

In accordance with one embodiment shown best in FIGS. 4 and 8, the shaft 159 can be coupled to the first connector arm 190 by a first biasing member 210. More specifically, the shaft 159 can include a mount structure 212 to which one end of the first biasing member 210 is attached, with the opposite second end of the first biasing member 210 being attached to the first connector arm 190. The first biasing member 210 can be in the form of a torsional spring that is wrapped (coiled) around a length of the shaft. The mount structure 212 can be in the form of a disk that is fixedly connected to the shaft 159 at a location adjacent an inner surface of the first linkage plate 160. One end of the torsional spring 210 can be fixedly attached to the disk 212 (which rotates in unison with the shaft 159) and the other end of the torsional spring 210 can be attached to the arm 195 of the first connector arm 190 (which does not move). As a result of this orientation, when the drive component 101 causes the shaft 159 to rotate in one direction, the spring 210 will begin to wind up and store energy. As described below, the torsional spring 159 transfers the motor rotation into a lifting and lowering of the apparatus 100.

Figure 7:
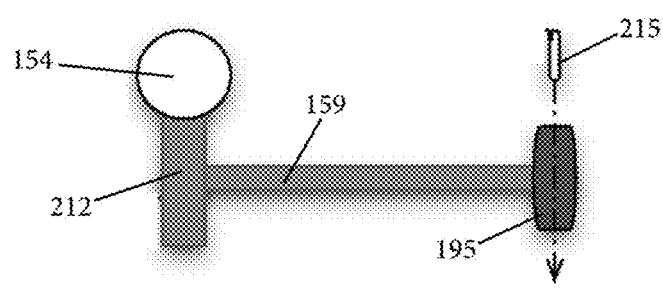
FIG. 7 is a front elevation view of a portion of a transmission of the device of FIG. 1 according to a first embodiment.

Alternatively, as shown in FIG. 7, the fixed pin 215 can be used to couple the shaft 159 to the first connector arm 190 so as to translate rotation of the shaft 159 (as a result of actuation of the motor) into the desired lifting and lowering of the apparatus 100.

It will be appreciated that the disk 212 can be initially disposed between the two linkage plates 160, 180 and the shaft 159 can be fed through the hole 170 in the plate 160 and then through a center hole in the disk 212 before then being passed through the respective holes formed in the second linkage plate 180 and the arms 195, 196. Any number of techniques can be used to fixedly attach the disk 212 to the shaft 160 including the use of fasteners, snap-fit mechanisms, etc. Both the disk 212 and the torsional spring 210 are thus disposed between the first linkage plate 160 and the arm 195.

The second connector arm 200 is similar to the first connector arm 190 and includes a base portion 201 (e.g., a horizontal bar) and a first pair of arms (flanges) 202 that extend outwardly from the base portion 201 at opposing ends thereof. The first pair of arms 202 are oriented perpendicular to the base portion 201 and are disposed in parallel planes such that in combination with the base portion 201, a first U-shaped structure is defined. The free ends of the arms 202 receive fasteners 205 for pivotally attaching the arms 202 to a body of the inspection vehicle 10. This allows the second connector arm 200 to pivot about the body of the inspective vehicle 10.

The second connector arm 200 also includes a plurality of arms that extend inwardly from the base portion 201 and locations intermediate the two ends of the base portion 201. As shown in the figures, a pair of inner arms 204 is formed between the ends of the base portion 201. The pair of inner arms 204 is formed perpendicular to the base portion 201 and is located in parallel planes. The planes that contain the first pair of arms 202 and the pair of inner arms 204 can be parallel to one another.

The free ends of the pair of inner arms 204 include through holes which receive a transverse shaft 207. The shaft 207 also passes through the holes 174, 188 formed in the first and second linkage plates 160, 180, respectively.

The shaft 207 freely rotates relative to the inner arms 204 and defines a pivot about which the second connector arm 200 can pivot. Fasteners 209 can be used to couple the shaft 207 to the inner arms 204 and restrict lateral movement of the shaft 207. These fasteners 209 can be bolts.

It will be understood that each of the first connector arm 190 and second connector arm 200 can be formed as a single, integral structure.

The first connector arm 190 defines a second link of the first linkage 102 and the second connector arm 200 defines a third link of the first linkage 102. The fourth link of the first linkage 102 is defined by the inspection vehicle 10 itself as described herein. The first linkage 102 can thus be characterized as a four bar linkage. Additional details concerning the operation of the first linkage 102 are set forth below.

The second linkage 103 serves to couple the sensor probe structure 104 to the first linkage 102 and allow the apparatus 100 to move in a different degree of freedom (other than the lifting and lowering action of the first linkage 102).

The sensor probe structure 104 consists of a casing or housing 300 for holding sensor 310. The housing 300 can be in the form of a box-like structure that has an open top and an open bottom. The housing 300 can have a square or rectangular shape. The housing 300 is thus defined by a pair of opposing side walls (front and rear walls) 302 and a pair of opposing end walls 304. End caps 305 can be used to close off the ends 304. A hollow interior space is defined between the walls 302, 304. The sensor 310 is rotatably disposed within this hollow interior space, with the sensor 310 being in the form of a wheel that rotates about an axle 301 that extends between the end walls 304/end caps 305. The sensor 310 has a diameter such that when the sensor probe (wheel) 310 is rotatably coupled to the axle 301, a portion of the sensor probe 310 extends both above the top edge of the housing 300 and below a bottom edge of the housing 300.

The axle 301 also supports one or more and preferably two wheels (rollers) 320 that further allow the apparatus to roll across and be steered across the surface 11 to allow inspection thereof. In the illustrated embodiment, the sensor probe (wheel) 310 is disposed between the pair of wheels 320. Similar to the wheels that are part of the inspection vehicle 10, the wheels 320 are preferably formed of a magnetic material to allow the apparatus 100 to attach to metal surface 11, such as a metal pipe or metal storage tank and be movable thereacross in response to driving of the inspection vehicle 10.

The second linkage 103 is similar to the first linkage 101 in that it is a four bar linkage configured to allow the apparatus 100 and in particular, the sensor probe 110 thereof, to move in response to applied forces as described herein. The second linkage 103 is formed of two pairs of cross link members and more specifically, the second linkage 103 is formed of first and second links 400, 410 which form a first pair and third and fourth links 420, 430 which form a second pair.

The first and second links 400, 410 are arranged in an X shape in that a first end of the first link 400 is pivotally attached to the first end surface 175 of the second section 165 of the first linkage plate 160 at a first pivot 401 and a second end of the first link 400 is pivotally attached to the side wall 302 of the housing 300 at a second pivot 403. Similarly, the second link 410 pivotally attached to the first end surface 181 of the second horizontal section 185 of the second linkage plate 180 at a third pivot 405 and a second end of the second link 410 is pivotally attached to the side wall 302 of the housing 300 at a fourth pivot 407.

As shown, the first and second links 400, 410 are not physically connected to one another.

Similarly, the third and fourth links 420, 430 are arranged in an X shape in that a first end of the fourth link 430 is pivotally attached to the second end surface 177 of the second section 165 of the first linkage plate 160 at a first pivot 421 and a second end of the fourth link 430 is pivotally attached to the other side wall 302 of the housing 300 at a second pivot 423. Similarly, the third link 420 pivotally attached to the second end surface 189 of the second horizontal section 185 of the second linkage plate 180 at a third pivot 425 and a second end of the third link 420 is pivotally attached to the other side wall 302 of the housing 300 at a fourth pivot 427.

As shown, the third and fourth links 420, 430 are not physically connected to one another.

In accordance with the present invention the first and second linkages along with the sensor probe structure 104 is configured such that the sensor 310 can be lowered or deployed against the surface 11 and automatically become normal to the surface 11 upon contact between at least a portion of the apparatus 100 and the surface 11 (e.g., in some embodiments, the sensor 310 itself can make contact with the surface 11 however this is not a requirement for the apparatus 100 to automatically normalize when contacting the surface 11). The first linkage 102 is actuated via the drive component 101 including the dampened worm gear transmission and the second linkage 103 allows for the passive normalization of the sensor probe 310 against the surface 11 as described herein. This mechanism provided by the present invention is particularly useful for sensitive directional sensors, such as a dry coupled probe which requires having its internal transducer component be always normal to the inspected surface in order to have proper readings from it.

When assembled, there is a space between the first and second linkage plates 160, 180 and the housing 300 in part to accommodate the wheels and sensor wheel.

Operation of the First Linkage

The first linkage 102 is configured to act as a lifter mechanism that allows the apparatus 100 to be raised and lowered, on command, relative to the surface 11. The interaction between the first linkage 102 and the drive component 101 thus adds one degree of freedom to the lifter mechanism in the vertical direction, thereby allowing the sensor probe 310 to be lifted up and placed down where and when needed. This degree of freedom maintains the integrity of the sensor probe 310 in a good shape by preventing it from dragging if a sideway motion is performed. Moreover, the drive component 101 provides the sensor probe 310 with sufficient compressing force on the inspected surface 11 for decent data acquisition.

The first linkage 102 operates as follows. When it is desired to deploy the sensor probe 310 against the surface 11, the user sends commands (instructions) to the drive component 101 causing actuation thereof. More particularly, the motor 110 is operated in a first mode of operation (to lower the sensor probe) causing the drive shaft 112 and the worm 152 to rotate in a first direction. The rotation of the worm 152 is translated into rotation of the worm gear 154. Since the transverse shaft 159 is fixedly connected to the worm gear 154, the shaft 159 also rotates. Rotation of the shaft 159 results in rotation of the disk 212 which is fixedly coupled thereto. The first biasing member (torsional spring) 210 is attached to both the disk 212 and the arm 195 of the first connector arm 190 and therefore rotation of the disk 212 (and shaft 159) results in a winding of the torsional spring 210 along the length of the shaft 159, whereby energy is stored.

The winding of the torsional spring 210 and its connection to the first connector arm 190 causes an upward force to be applied to the first connector arm 190. Since the first connector arm 190 is pivotally attached to both the inspection vehicle 10 and the first and second linkage plates 160, 180, the first connector arm 190 pivots in an upward direction. The sensor probe 310 is lifted up from the surface 11 since the sensor probe 310 is carried by the housing 300 which itself is connected to the first linkage 102 (by means of the second linkage 103). The upward movement of the housing 300 causes the sensor probe 310 to lift from the surface 11.

To lower the sensor probe 310, the operation is reversed in that the motor 110 is operated in a second mode of operation to cause the drive shaft 112 and the worm 152 to rotate in a second direction which is opposite the first direction. The torsional spring 210 unwinds along the shaft 159 and this results in the first connector arm 190 moving in a downward direction, thereby lowing the housing 300 and sensor probe 310 resulting in the sensor probe 310 making contact with surface 11 in the illustrated embodiment.

This torsional spring 210 thus acts as a linear coil that transfers the rotation of the motor 110 and is used as a torsional spring acting on the first linkage 102. The coil (spring 210) generates a damping effect between the sensor probe 310 and the surface 11. Thus, when moving the sensor probe 310 on a rough or uneven surface, the torsional spring 210 minimized the damage and disturbance caused by the pressure on the sensor. In other words, when moving the sensor probe 310 on slightly uneven surfaces, the sensor probe 310 maintains contact without disturbing the motion of the apparatus 100. The damping effect of the spring 210 provides an advantage over the fixed pin design, shown in FIG. 7, in that the fixed pin design does transform the rotation motion of the motor 110 into a vertical linear motion/force via the first linkage 102, the fixed pin design lacks a damping effect.

It will be understood that, other techniques beyond the ones shown in the figures can be used to couple the shaft 159 to the first connector arm 190 in such a way that the rotation motion of the motor 110 in translated into a vertical linear motion/force of the apparatus 100 via the first linkage 102.

In addition, it will be understood that the apparatus itself can be configured to maintain contact with the surface 11 during motion of the apparatus 100 over the surface 11. In other words, the object carried by the apparatus 100 may not contact the surface but instead a portion of the apparatus 100 (such as the second linkage) acts to normalize upon contact with the surface 11 and maintains such contact with surface 11 when the apparatus 100 moves along the surface 11.

Connector Arms of Different Lengths

In one embodiment, the first and second connector arms 190, 200 can have different lengths. With reference to FIGS. 12A-C, given the specific placement of the apparatus 100 relative to the body of the external device 10 (e.g., an inspection vehicle) and the anatomy of the external device 10, the probe 310 contacts the surface 11 at a different height depending on the curvature of the surface 11. The result is that since the first stage (first linkage) is configured to move the probe 310 along a curved path instead of along a rectilinear one, the contact angle (on the pitch direction) between the probe 310 and the surface 11 can be optimized to be near perfectly normal. In other words, this difference in lengths will determine whether the first stage of the apparatus 100 is configured for rectilinear motion or for motion along a curved path. As described herein, the actuator (drive motor) is configured to move along a curved path and the drive motor has a dual purpose: lifting/lowering of the probe as well as normalization of the probe against the surface in the pitch direction.

FIG. 12A shows the surface 11 being a flat surface and the apparatus 100, including connector arms 190, 200 is shown along with inspection vehicle 10. In FIG. 12A, it is seen that the angle between the probe 310 and the surface 11 is about 89.6° (i.e., normalization in the pitch direction is nearly perfect).

FIG. 12B shows the surface 11 being in the form of an 8 inch pipe and the relative positions of the apparatus 100, including connector arms 190, 200 is shown along with inspection vehicle 10. In FIG. 12B, it is seen that the angle between the probe 310 and the surface 11 is about 180.1° (i.e., normalization in the pitch direction is nearly perfect).

FIG. 12C shows three examples for the construction of the surface 11 in that the surface 11 is shown as being a flat surface (FIG. 12A); 8 inch pipe (FIG. 12B); and a 13 inch pipe. In FIG. 12C, it is seen that the angle between the probe 310 and the surface 11 is about 181.9° in the case of the 13 inch pipe (i.e., normalization in the pitch direction is nearly perfect).

As described herein, the apparatus 100 is preferably configured such that the probe is at least substantially normalized in an automated manner during normal use of the apparatus. As used herein, the term substantially normalized means the probe is positioned within at least 5 degrees of perfect normalization relative to the surface and preferably is positioned within at least 3 degrees of perfect normalization and more preferably is positioned within at least 2 degrees of perfect normalization and in some embodiments is positioned within at least 1 degree of perfect normalization (see FIGS. 12A and 12B).

Operation of the Second Linkage

The second linkage 103 is designed to control the roll configuration of the sensor probe 310 and thus, provides the apparatus with a second degree of freedom obtained by adding a passive joint to the apparatus 100. FIGS. 9A and 9B illustrate a passive joint according to one embodiment and FIGS. 10A and 10B illustrate a passive joint according to another embodiment. The passive joint shown in FIGS. 10A and 10B can be thought of as being a T-shaped joint (swinging pendulum). When a force is applied to the housing 300 (which carries the sensor probe 310), the housing 300 pivots about a single pivot point to cause displacement of the housing 300 and the sensor probe 310.

Figure 2:
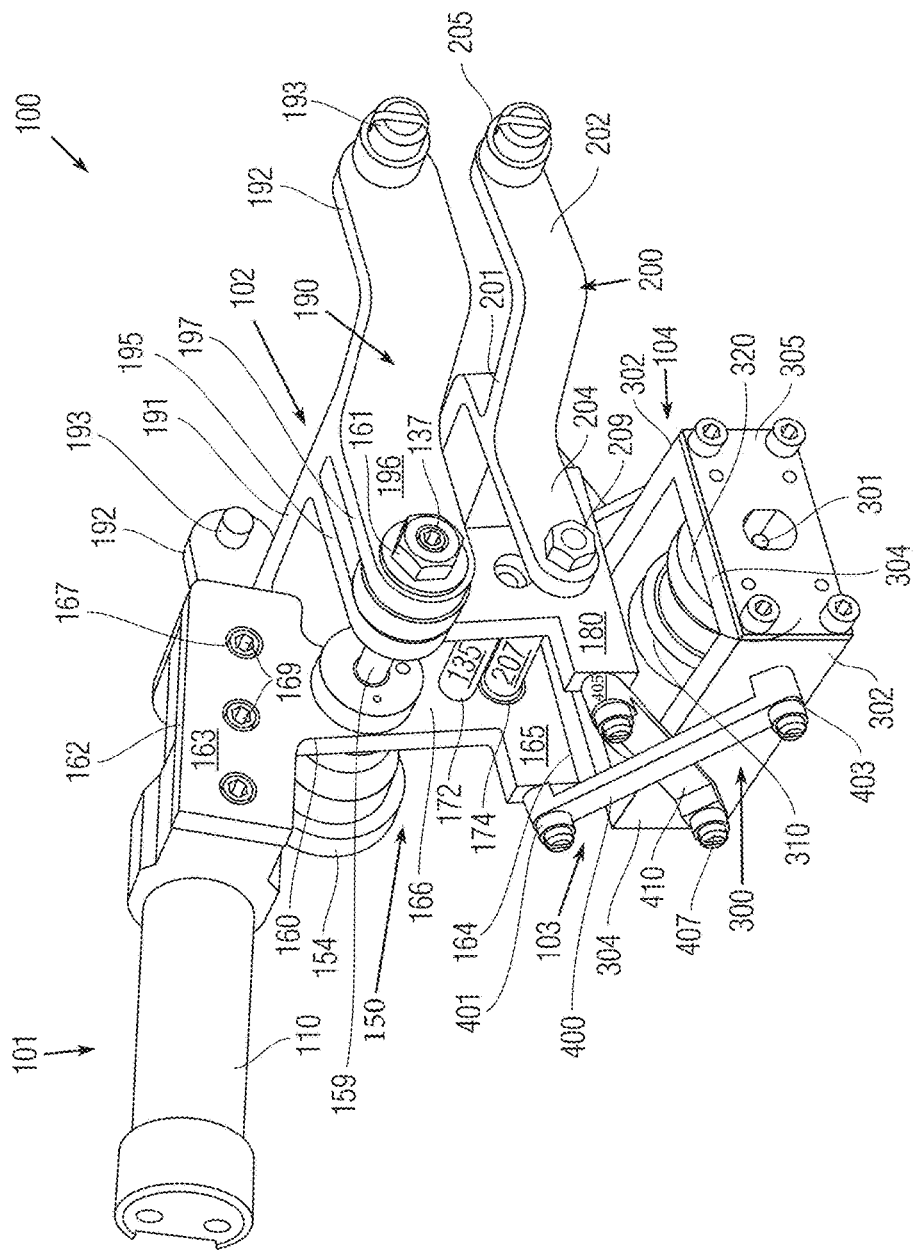
FIG. 2 is a side perspective view of the device of FIG. 1.

In accordance with the present invention and as shown in the figures including FIGS. 9A and 9B, the second linkage 103 is in the form of an X-shaped four bar linkage which is utilized and designed to set as low and as close as possible to the surface 11 (metal surface), the remove center of rotation of the sensor axis. FIGS. 9A and 9B show the movement of the housing 300 and sensor probe 310 in response to the force (F) being applied and a comparison between FIGS. 9A and 9B (X-shaped) and FIGS. 10A and 10B (T-shaped) show that the center of rotation is lower in the X-shaped design to the location of the multiple pivots thereof as compared to the location of the single pivot in the T-shaped. With reference to FIG. 2, the horizontal displacement of the sensor probe 310 when using the X-linkage 103 is considerably less than the displacement obtained when using a normal degree of freedom with one higher center of rotation (See embodiment of FIGS. 10A and 10B). When comparing the embodiment of FIGS. 9A and 9B (X-shaped) to the embodiment of FIGS. 10A and 10B, one finds that the horizontal displacement of the X-shaped design is about half (½) of the horizontal displacement of the T-shaped link design.

Figure 11B:
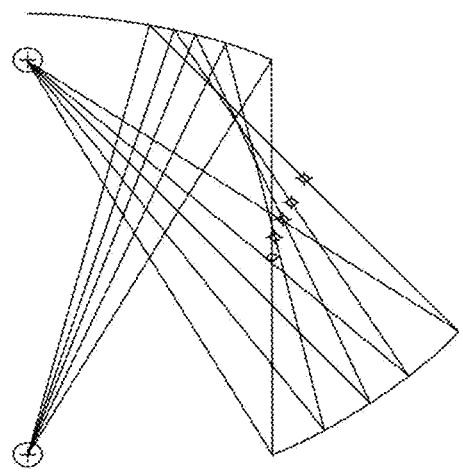
FIGS. 11A and 11B show a chart comparing a trajectory of a sensor probe that is part of the conventional T linkage (FIG. 11A) versus a sensor probe that is part of the second linkage (FIG. 11B)
Figure 11A:
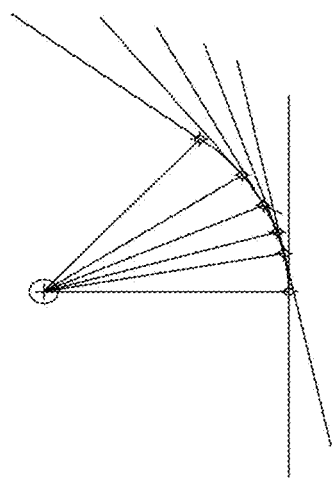

Furthermore and with reference to FIGS. 11A and B, the X link mechanism (second linkage 103) because of the two passive joints it possesses generates a trajectory for the contact point of the sensor probe 310 that moves downward with the rotation of the housing 300 (and sensor probe 310), while in the case of the T joint, shown in FIGS. 10A and 10B, the contact point moves upward. This difference in motion is clearly seen in the graph presented in FIGS. 11A and B and more specifically, in FIGS. 11A and B, the trajectory relative to the T-link is shown in FIG. 11A and the trajectory relative to the X-link is shown in FIG. 11B. This difference in trajectories illustrates the advantage of using an X-link in that the X-link mechanism tends to generate a more stable contact point by compressing the sensor probe 310 toward the metal surface 11, while in the case of a T-joint, the sensor probe 310 tends to escape and lose eventually the contact point. This feature is especially useful when moving over pipes and in particular when following a helix like trajectory.

In accordance with the present invention, the X-shaped linkage (second linkage 103) plays an important role in closely aligning the sensor probe 310 to the normal axis of the inspected surface 11. The inclusion of the two rollers (wheels 320) provides increased normalization with one wheel 320 on each side of the sensor probe 310. When an appropriate force is exerted on the mechanism, the two rollers (wheels 320) eventually touch the surface 11 and act as a support for the sensor probe 310 which in turn normalizes the sensor probe 310 on the surface 11.

Figure 3:
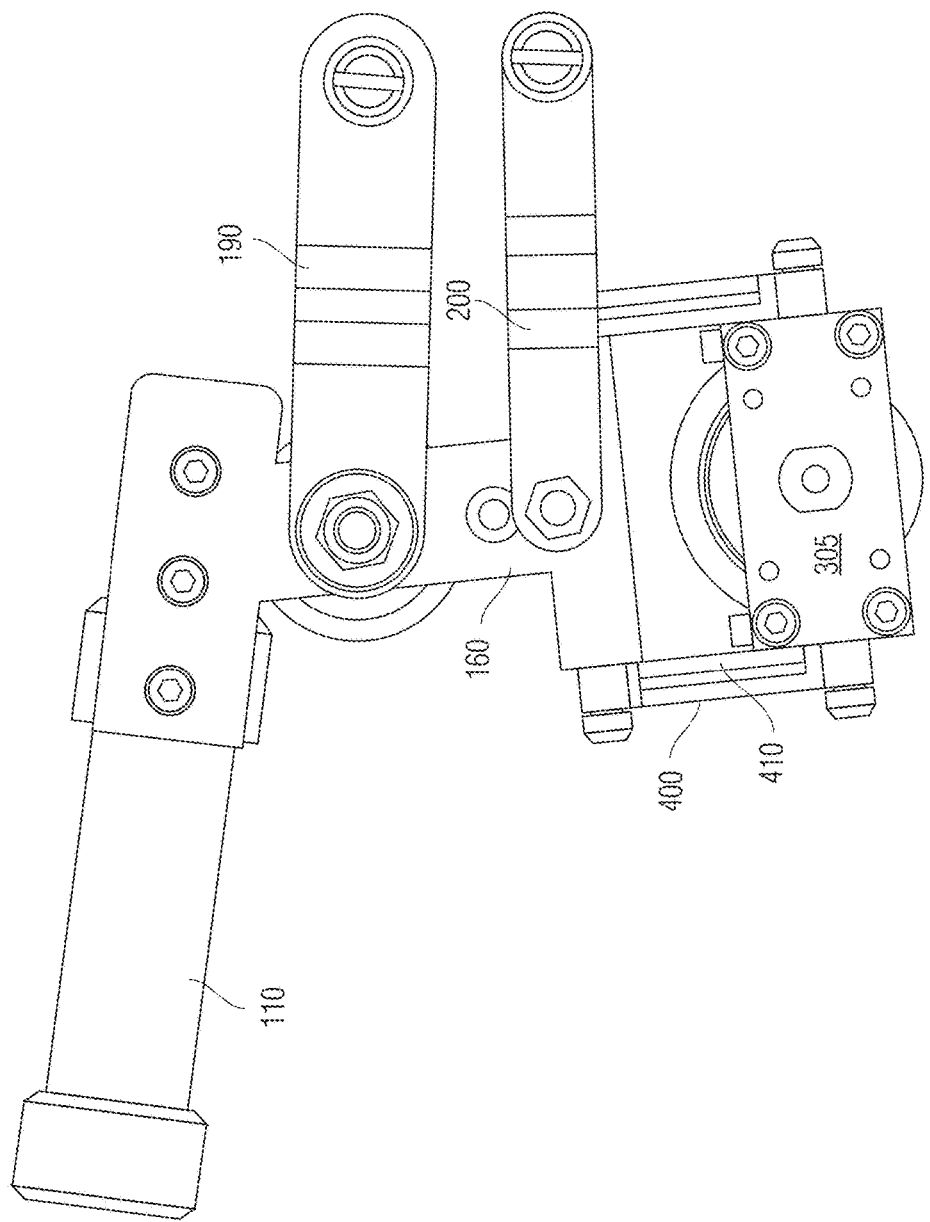
FIG. 3 is a side elevation view of the device of FIG. 1 showing a first linkage.

In one application of the present invention and in order to perform ultrasonic inspection to measure a wall thickness (e.g., thickness of a pipe wall or storage wall), the sensor probe 310 is in the form of a dry coupled probe (DCP) in order to avoid carrying couplant onboard. As mentioned herein, normal contact has to be achieved between the pipe surface and sensor probe 310 to receive the emitted ultrasonic waves and to acquire a clean thickness signal (in this case when the sensor probe 310 makes contact with the surface 11—in other embodiments, the normal contact is between the frame (e.g., the second mechanism) carrying the sensor and the surface). To achieve this normalization, the apparatus 100 of the present invention provides a two stage mechanism with two degrees of freedom. The first stage comprises the first linkage 102 has a planar degree of freedom when looked at from the side as shown in FIG. 3. This first stage can play two rules, namely, it allows the sensor probe 310 to be lowered and raised to target different pipe curvatures by spring loading to make sure the sensor probe 310 is pressed against the surface 11. It also lifts the sensor probe 11 off of the surface 11 to avoid damage. The damping effect described herein allows the sensor to maintain contact without disturbing the motion of the inspection vehicle 10 (robot) when the sensor probe 10 is traveling on slightly uneven surfaces. The DCP sensor probe (wheel) 310 can be configured to have a passive dampened motion within the inner diameter of the support rollers 320 by accounting for desired pressure for the sensor probe 310 during inspection.

In addition and when the sensor 310 is in the form of a rubber wheel sensor probe, the present applicant observed that the stiffness of the probe rubber needs to be accounted for in the design of the lifter mechanism for an optimal performance. This stiffness will drive design parameters such as the diameter of the roller bearings on the sides of the probe sensor 310 and/or the placement of the sensor probe relative to the contact rollers 320. For example, the diameters of the rollers 320 and their placement relative to the probe 310 is preferably optimized to make sure that the probe 310 is under about 1 to 2 Kgs of pressure by the time the two rollers 320 make contact with the surface 11. Alternatively, the roller 320 around the sensor probe 310 can be magnetized. The magnetic rollers 320 assist the normalization of the probe 310 by ensuring perfect contact of the rollers 320 with the surface 11. The rollers 320 are preferably constructed such that the rollers 320 do not product much attraction force towards the surface 11; otherwise, the mechanism (first linkage 102) may have difficulty in lifting the sensor probe 310 after the inspection is completed. In addition, the rollers can be made to have a slimmer profile relative to the sensor probe 310 and a spring load can be added between the rollers 320 and the sensor probe 310 to introduce a damping effect while moving on uneven surfaces.

Thus, in accordance with the present invention, the diameter of the support rollers 320 is selected by accounting for the stiffness of the probe material as well as the desired pressure for the probe during inspection. An offset can also be introduced between the axis of the sensor probe wheel 310 and the support rollers 320 by accounting for the stiffness of the probe material as well as the desired pressure for the probe during inspection.

On other embodiments, the rollers 320 make contact with the surface 11

The second stage made up of the second linkage 103 provides a second degree of freedom when viewed toward the rear as shown in FIG. 4. This allows the sensor probe 310 to adjust to pipe inclination when the inspection vehicle 10 is driving in a helical path instead of circumferentially or longitudinally. As discussed herein, this degree of freedom is passive. The two rollers 320 sitting on either side of the sensor probe 310 support the sensor probe and force the mechanism to normalize when the sensor probe 310 gets in contact with the surface 11.

It will be understood that the present invention covers an apparatus which holds a sensor and includes at least two degrees of freedom for performing the operations described herein. One degree of freedom is associated with an active mechanism (active linkage) which is configured to raise and lower the sensor (vertical movement) and another degree of freedom is associated with a passive mechanism which normalizes the sensor.

The sensor holding apparatus 100 of the present invention provided a number of advantages not found in conventional competing products and overcomes the deficiencies associated with the prior art. More specifically, the following advantages are obtained with the apparatus of the present invention:

Probe damage from lateral drag: Previous devices in the prior art are designed to constantly apply pressure between the DCP wheel and the surface, meaning there is no way of lifting the probe from the surface other than by removing the entire device from it. The first 4-bar linkage mechanism (linkage 102) of the present apparatus is attached to a worm-geared motor that allows the probe to be lifted from the surface. This is particularly important for inspection robots because the robot needs to steer sideways and the DCP wheel probe would be damaged if dragged sideways on the surface.

Pitch normalization & probe deployment via single actuator, not two: The prior art discloses the general use of 4-bar linkages to deploy probes typically moving them along a rectilinear path towards and away from the surface. However, the prior art fails to address the proper normalization of the probe in the "pitch" direction via this linkage implicitly introducing the need for a second actuator to add an additional degree of freedom to the probe mounting for normalization. Nevertheless, the proposed invention is distinguished from prior art in the sense that it introduces a customized design for the components of the first 4-bar linkage such that the probes moves along a curved path rather than along a straight line, such that the probe is automatically normalized as it is deployed (at least in the "pitch" direction) without need for a second actuator. However, as discussed previously, it will be appreciated that the mechanism disclosed herein can be employed without the use of actuator and instead, employ a biasing element or the like that ensures that the probe is always deployed against the surface.

Reliable constant pressure against the surface: The prior art requires manual handling of the scanning head to ensure sufficient force is exerted on the probe against the surface. The four bar link mechanism in the present apparatus, attached to a torsional spring, allows the probe to be lowered and pressed against curved/flat surfaces. The support rollers on the sides of the probes allow for a reliable constant pressure to be applied on the probe.

Normalization of the probe in the "roll" direction: Driving helically along a pipe with proper probe normalization hasn't been addressed in prior art. The X-link mechanism supported by the pressure from the four bar link mechanism on top (first linkage 102) allows one degree of freedom for the probe to approach the normal axis of the curved surface. Along with sufficient pressure, good UT readings are acquired.

It will therefore be appreciated that the present apparatus can be configured to carry and instrument or probe and optionally deploy it against a surface. The present apparatus is very effective at carrying any type of object that has to be deployed against and/or eventually retrieved from a curved surface while ensuring that the object is pointing straight at the surface. This can be achieved with a single actuator.

While the present apparatus is described as being used for carrying a probe, this is merely one exemplary application for the present apparatus and it can carry other objects, including not limited to a laser, other types of sensors, such as an infrared sensor, a camera, etc. For example, the apparatus can carry a laser or infrared sensor that is configured to run on transparent PVC pipes or curved glass panels. The apparatus can be driven or otherwise moved along the transparent pipe and by matching the signatures found in the measured signals, the apparatus can calculate which product is flowing within the pipe. The product can come in any number of different forms, such as a liquid or gas, etc. For example, the product can be crude oil or different types of gases. Similarly, if the present apparatus carried a camera or other imaging equipment, then the apparatus can be used in at least several different ways. First, it can be used on transparent materials as mentioned above and can take one or a series of images (close-up photos, etc.) of whatever is going on inside the transparent surface or second, if the imaging device (camera) is rotated 90 degrees, then it would be pointing not normal to the surface but nearly tangential to it and this allows the device to perform a very nice close-up visual inspection of any material.

While the present invention has been described above using specific embodiments, there are many variations and modifications that will be apparent to those having ordinary skill in the art. As such, the described embodiments are to be considered in all respects as illustrative, and not restrictive. Therefore, the scope of the invention is indicated by the appended claims, rather than by the foregoing description. All changes that come within the meaning and range of equivalency of the claims are to be embraced within their scope.

What is claimed is:

1. A system for deploying an inspection device in a normalized orientation relative to a surface, the system comprising:
    an instrument configured to inspect the surface;
    an apparatus comprising:
        a first linkage operatively coupled to the instrument and configured to move the instrument in a first direction and according to a first path relative to the surface, and
        a second linkage operatively coupled to the instrument and configured to move the instrument according to a second direction to cause the instrument to become normal to the surface upon contact between at least a portion of the apparatus and the surface,
        wherein the first linkage comprises a first four bar linkage and the second linkage comprises a second four bar linkage; and
    an external device attachably coupled to the apparatus and configured to controllably move over the surface.

2. The system of claim 1, wherein the instrument comprises a sensor probe for inspecting the surface and at least the second linkage is in contact with the surface to cause the sensor probe to become normal to the surface.

3. The system of claim 2, wherein the sensor probe comprises a rotatable wheel that is mounted within a housing and is disposed between a pair of support rollers that are also rotatable within the housing.

4. The system of claim 3, wherein the support rollers are magnetized to ensure contact between the rollers and the surface.

5. The system of claim 1, further comprising a motor that is operatively coupled to the first linkage for actively driving the first linkage so as to move the instrument according to the first path, wherein the first path comprises a lifting and lowering of the instrument relative to the surface.

6. The system of claim 5, wherein the second linkage is passive in nature and automatically moves the instrument in the second direction without action by the motor.

7. The system of claim 6, wherein the normalization of the instrument to the surface upon contacting the surface is automatic due to a passive nature of the second linkage which is free of direct connection to the motor.

8. The system of claim 5, wherein the motor is operatively coupled to the first linkage by a transmission.

9. The system of claim 8, wherein the transmission comprises a worm drive defined by a worm that is connected to a drive shaft of the motor and a worm gear that is connected to a worm gear shaft which is coupled to the first linkage such that rotation of the worm gear shaft is translated into the instrument moving according to the first path.

10. The system of claim 8, further comprising a dampening coil that couples the transmission to the first linkage.

11. The system of claim 8, wherein the transmission is rigidly coupled to the first linkage with a pin.

12. The system of claim 1, wherein the instrument comprises an ultrasonic probe.

13. The system of claim 12, wherein the ultrasonic probe comprises an ultrasonic dry coupled wheel probe.

14. The system of claim 1, wherein first four bar linkage is configured such that the instrument moves along a curved path that represents the first path rather than along a straight line such that the instrument is automatically normalized, at least in a pitch direction, as the instrument is deployed and makes contact with the surface.

15. The system of claim 1, wherein the second four bar linkage has an X shape and is pivotally coupled to both a housing holding the instrument and to the first four bar linkage.

16. The system of claim 1, wherein the second four bar linkage is disposed below the first four bar linkage and is configured to normalize the instrument in a roll direction relative to the surface.

17. The system of claim 1, further including an actuator operatively coupled to the first linkage for moving the first linkage so as to move the instrument according to the first path, wherein the first four bar linkage comprises a first linkage plate that is fixedly connected to the actuator; a second linkage plate that is fixedly connected to and spaced from the first linkage plate; a first connector arm pivotally connected to the first and second linkage plates and configured for being pivotally attached to the inspection vehicle; and a second connector arm pivotally connected to the first and second linkage plates and configured for being pivotally attached to the inspection vehicle, wherein the first connector arm is coupled to an actuator, that is operatively connected to the first linkage, such that rotation of the actuator is translated into the first connector arm being raised or lowered relative to the surface, whereby the instrument is also raised or lowered relative to the surface.

18. The system of claim 1, wherein the second four bar linkage comprises:
    a first link pivotally attached to the first four bar linkage and to a housing holding the instrument;
    a second link pivotally attached to the first four bar linkage and to the housing holding the instrument;
    a third link pivotally attached to the first four bar linkage and to the housing holding the instrument; and
    a fourth link pivotally attached to the first four bar linkage and to the housing holding the instrument, wherein the first and second links are arranged so as to have an X shape and are disposed along a front of the housing and the third and third and fourth links are arranged so as to have an X shape and are disposed along a rear of the housing.

19. The system of claim 1, wherein the external device is an inspection vehicle comprising a processor configured to receive and record information received from the instrument.

* * * * *